United States Patent
Lomholt

(10) Patent No.: US 7,073,503 B2
(45) Date of Patent: Jul. 11, 2006

(54) RESPIRATION CATHETER WITH SEALING CUFF AND GAS INFLATION CUT-OFF VALVE

(76) Inventor: Vagn Niels Finsen Lomholt, Lars Nielsens Voj 4, DK-2970 Hørsholm (DK)

(*) Notice: Subject to any disclaimer, the term of this patent is extended or adjusted under 35 U.S.C. 154(b) by 0 days.

(21) Appl. No.: 11/149,215

(22) Filed: Jun. 10, 2005

(65) Prior Publication Data

US 2005/0274382 A1 Dec. 15, 2005

(30) Foreign Application Priority Data

Jun. 11, 2004 (DK) ............................... 2004 00908

(51) Int. Cl.
*A61M 16/00* (2006.01)
(52) U.S. Cl. ............................. 128/207.15; 128/200.26
(58) Field of Classification Search .......... 128/200.26, 128/207.14, 207.15; 604/99.01
See application file for complete search history.

(56) References Cited

U.S. PATENT DOCUMENTS

| | | | | |
|---|---|---|---|---|
| 2,792,837 A | * | 5/1957 | Kardos | 128/207.15 |
| 3,211,152 A | * | 10/1965 | Stern | 128/207.15 |
| 3,460,541 A | * | 8/1969 | Doherty | 128/207.15 |
| 3,481,339 A | * | 12/1969 | Puig | 128/207.15 |
| 3,504,676 A | | 4/1970 | Lomholt | |
| 3,794,036 A | * | 2/1974 | Carroll | 128/207.15 |
| 3,995,643 A | * | 12/1976 | Merav | 128/207.15 |
| 4,020,849 A | * | 5/1977 | Jackson | 128/207.15 |
| 4,046,139 A | * | 9/1977 | Horn | 600/549 |
| 4,285,340 A | * | 8/1981 | Gezari et al. | 128/205.24 |
| 4,850,371 A | * | 7/1989 | Broadhurst et al. | 600/532 |
| 4,967,759 A | * | 11/1990 | Teves | 600/528 |
| 5,311,864 A | * | 5/1994 | Huerta | 128/207.15 |
| 5,497,768 A | | 3/1996 | Lomholt | |
| 6,745,773 B1 | * | 6/2004 | Gobel | 128/207.15 |

FOREIGN PATENT DOCUMENTS

DK C-111149 6/1968

* cited by examiner

*Primary Examiner*—Aaron J. Lewis
(74) *Attorney, Agent, or Firm*—Hunton & Williams LLP

(57) ABSTRACT

A respiration catheter has a sealing cuff (12) which encircles the catheter tube (10) and can be connected through a separate cuff inflation tube (14) with a source of compressed air with a substantially constant pressure. The cuff has a collar at both ends of the cuff. The cuff inflation tube (14) has an opening (17) below the collar of the cuff (13) in the vicinity of the free end of the catheter. A thin-walled part of the collar (15) covers the inlet of the cuff inflation tube into the cuff, and functions as a cut-off valve which is controlled by the pressure of the respiration air and is adapted to prevent air in the sealing cuff from escaping when this pressure exceeds the pressure in the source of compressed air.

4 Claims, 1 Drawing Sheet

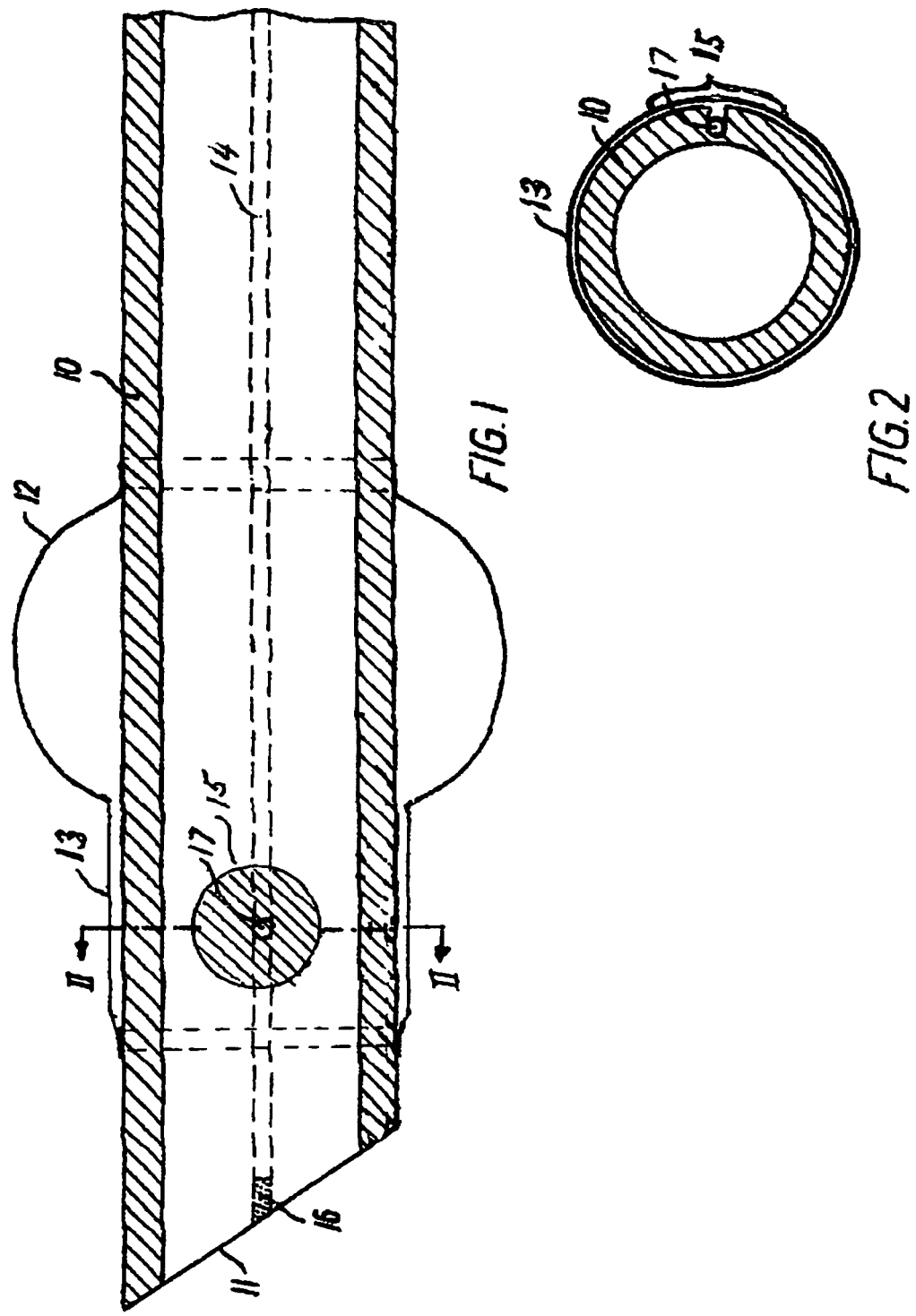

RESPIRATION CATHETER WITH SEALING CUFF AND GAS INFLATION CUT-OFF VALVE

CROSS-REFERENCE TO RELATED APPLICATIONS

This application claims the benefit of Denmark patent application PA 2004 00908, filed on Jun. 11, 2004, which is incorporated herein by reference.

The invention concerns a respiration catheter comprising a respiration tube for insertion into a patient's trachea.

BACKGROUND OF THE INVENTION

Endotracheal tubes intended for insertion through the mouth, nose or implanted in the neck (oro-naso and tracheostomy tubes) are usually provided with an inflatable cuff for sealing against the tracheal wall. The efficiency of the sealing is determined by the magnitude of the cuff pressure against the tracheal wall since the inflated cuff does not seal off pressures exceeding the pressure of the cuff against the wall. The air pressure in the cuff determines the pressure against the tracheal wall. The pressure of the cuff against the tracheal wall can be controlled and regulated only if the cuff has a sufficiently large diameter to make contact with the tracheal wall without stretching of the sheet material of the cuff, i.e. the cuff must be lying folded on the tracheal wall. If this demand is met, the pressure in the cuff is identical with its pressure on the wall.

If the pressure of the cuff against the tracheal wall is considerably higher than 30 cm $H_2O$, the blood supply to the mucosa is occluded, and this causes damage in the form of superficial and deeper ulcerations after some time. This damage is prevented in that the sealing cuff, lying folded on the wall, is kept inflated from an outer source with a constant, regulated pressure of 20 to 30 cm $H_2O$.

The sealing cuff has the additional function of preventing liquid (blood, saliva, vomit) from flowing past the cuff down into the lungs. It has been found that this function is accomplished when the pressure of the sealing cuff against the tracheal wall is at least 20 to 30 cm $H_2O$.

Spontaneous changes in the diameter of the trachea, changes in the catheter position and the diffusion of certain anaesthetic gases through the wall of the sealing cuff may cause considerable changes in the pressure in the sealing cuff if the pressure is not controlled and regulated.

During artificial respiration the necessary pressure of the respiration air may often exceed 20 to 30 cm $H_2O$, and the pressure in the sealing cuff without a valve is then too low to seal off the pressure of the respiration air.

In order for the sealing cuff to be able to seal off high inflation pressures during artificial respiration, the respiration catheter described in DK-C-111149 is equipped with a two way cut-off valve mounted on the air supply tube for sealing the cuff. Due to the flow resistance between the two ends of the catheter and consequent difference in pressure, the valve closes prematurely and opens prematurely. This entails that part of the air in the sealing cuff escapes during the expiratory phase so that, for a short moment, the cuff can not provide an efficient sealing of the trachea.

The respiration catheter described in U.S. Pat. No. 5,497,768 has a cut-off valve outside the cuff in the vicinity of the free end of the catheter. The valve membrane is an elastic membrane along the circumference of the catheter covering the inlet and the outlet of the cuff inflation tube. When, during inflation of the lungs, the pressure in the airway downstream in relation to the cuff exceeds the pressure in the cuff inflation tube, the valve is in the closed position and prevents air from escaping from the cuff. When the pressure in the airway decreases below the pressure in the cuff inflation tube during expiration, the valve is in the open position and allows the pressure in the cuff to equilibrate with the outside pressure source. The potential risk inherent with the design is the valve membrane being disengaged and lost into the lungs.

SUMMARY OF THE INVENTION

According to the present invention, a respiration catheter is provided comprising a sealing cuff, said cuff having inflation means comprising a source of pressurized gas and a cuff inflation tube, said cuff inflation tube further comprising an opening into the cuff, said opening being placed under the collar of the cuff in the vicinity of the free end of the catheter, a part of the collar covering the opening of said cuff inflation tube into the cuff being thin-walled, said thin-walled part of the collar being responsive to pressure of respiratory gas downstream of said cuff and functions as a cut-off valve, said cut-off valve having a first position and a second position, said first position comprising an open position with pressurized gas communicating through said inflation tube to said cuff, said second position comprising a closed position with communication of pressurized gas between said source of pressurized gas and said cuff being interrupted, said cut-off valve assuming said second position responsive to a pressure in the respiratory gas downstream of said cuff exceeding gas pressure in said inflation tube, said thin-walled part of the collar may be a circular part of said collar centred on said opening of said inflation tube into said cuff, said thin-walled part of said collar may be encircling said catheter where said opening of said inflation tube is positioned, said thin-walled part of the collar may be a different material from the material of the cuff.

The thin-walled part of the collar may be a circular part of said collar centered on said opening of said inflation tube into said cuff.

The thin-walled part of said collar may encircle said catheter where said opening of said inflation tube is positioned.

The thin-walled part of the collar of said cuff may be of a material different from the material of said cuff.

BRIEF DESCRIPTION OF THE FIGURES

A preferred embodiment of the invention will now be described with reference to the figures as follows:

FIG. 1 is a partly longitudinal cross-sectional view of a respiration catheter in accordance with the present invention, FIG. 2 is a cross-sectional view of the respiration catheter along line II—II shown in FIG. 1.

DETAILED DESCRIPTION OF THE FIGURES

In the figures 10 is a catheter tube intended for introduction into a patients trachea. Close to oblique cut end 11 of the tube 10 is placed a sealing cuff 12, which is made from thin sheet material and encircles the tube. Compressed air can be supplied to the cuff through a channel 14, which is provided in the wall of the catheter tube 10, and which is closed by plug 16 at the end of tube 10. The channel 14 has a hole 17, which communicates with the inside of the cuff 12. The hole 17 is positioned below the collar 13 of the cuff. The part of the collar 13 of the cuff, which covers the opening 17 in the inflation tube 14, is thin-walled sheet material. The channel 14 can be connected to a source of compressed gas (not shown), which delivers air with a substantially constant pressure, which may be of the order of 20 to 30 cm of $H_2O$.

When the shown catheter is introduced into a patient's trachea, air is conducted from a source of compressed air through the channel 14 to the cuff 12, which is thereby inflated and establishes sealing engagement with the wall of the trachea. The pressure applied for this purpose is so low that it cannot damage the mucosa of the trachea. When, during blowing of respiration air, the pressure in the trachea exceeds the pressure in the cuff, the thin-walled part of the collar of the cuff 15 closes the hole 17 so that the air in the cuff cannot escape. The respiration pressure now acts on the cuff side facing the lungs and increases the engagement pressure of the cuff. This increased engagement pressure, which may be damaging if applied for a prolonged period, is applied only during the short periods when the respiration pressure reaches its maximum.

Accordingly, the respiration catheter of the invention ensures effective sealing against the tracheal wall under all circumstances, also in the case of lungs of low compliance requiring high respiration pressures, and also ensures full perfusion of the tracheal wall since the engagement pressure is below the value which may cause damage, except for shorter periods.

The cut-off valve may also be constructed differently from what is described and may e.g. be formed by a sleeve or a bladder of thin material surrounding the catheter tube.

The invention claimed is:

1. A respiration catheter tube for insertion into a patient's trachea, said catheter tube including a sealing cuff, said cuff comprising inflation means comprising a source of pressurized gas and a cuff inflation tube, said cuff inflation tube further comprising an opening into the cuff, said opening being placed under a collar of the cuff in the vicinity of a free end of the catheter, a part of the collar covering the opening of the cuff inflation tube into the cuff being thin-walled, said thin-walled part of the collar being responsive to pressure of respiratory gas downstream of said cuff, said thin-walled part of the collar having a first position and a second position, said first position comprising an open position with pressurized gas communicating through said inflation tube to said cuff, said second position comprising a closed position with communication of pressurized gas between said source of pressurized gas and said cuff being interrupted, said thin-walled part of the collar assuming said second position responsive to a pressure in the respiratory gas downstream of said cuff exceeding gas pressure in said inflation tube.

2. A respiration catheter according to claim 1, wherein said thin-walled part of the collar is a circular part of said collar centered on said opening of said inflation tube into said cuff.

3. A respiration catheter according to claim 1 wherein said thin-walled part of said collar is encircling said catheter where said opening of said inflation tube is positioned.

4. A respiration catheter according to claim 1, wherein said thin-walled part of the collar of said cuff is a material different from the material of said cuff.

* * * * *